(12) United States Patent
Vincent et al.

(10) Patent No.: US 8,685,090 B2
(45) Date of Patent: Apr. 1, 2014

(54) AUDITORY OSSICLE PROSTHESIS WITH STABILISER ELEMENT

(75) Inventors: Robert Vincent, Beziers (FR); Uwe Steinhardt, Hirrlingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 106 days.

(21) Appl. No.: 13/357,670

(22) Filed: Jan. 25, 2012

(65) Prior Publication Data
US 2012/0197394 A1 Aug. 2, 2012

(30) Foreign Application Priority Data
Jan. 29, 2011 (EP) .................................... 11000723

(51) Int. Cl.
*A61F 2/18* (2006.01)
(52) U.S. Cl.
USPC ............................................ 623/10; 600/25
(58) Field of Classification Search
USPC ............................................ 623/10; 606/25
See application file for complete search history.

(56) References Cited

U.S. PATENT DOCUMENTS

| 4,130,905 | A | * | 12/1978 | Mercandino | .................... 623/10 |
| 4,169,292 | A | | 10/1979 | Grote | |
| 4,728,327 | A | | 3/1988 | Gersdorff | |
| 7,628,812 | B2 | * | 12/2009 | aWengen et al. | ............... 623/10 |
| 2004/0162614 | A1 | * | 8/2004 | Steinhardt et al. | ............... 623/10 |
| 2007/0255405 | A1 | * | 11/2007 | Reitan et al. | .................... 623/10 |
| 2009/0149697 | A1 | * | 6/2009 | Steinhardt et al. | ............... 600/25 |
| 2009/0164010 | A1 | | 6/2009 | Steinhardt et al. | |
| 2009/0240332 | A1 | * | 9/2009 | Steinhardt et al. | ............... 623/10 |
| 2010/0191331 | A1 | * | 7/2010 | Steinhardt et al. | ............... 623/10 |

FOREIGN PATENT DOCUMENTS

| DE | 20 2008 003 887 | 6/2008 |
| DE | 10 2007 041 539 | 3/2009 |
| EP | 0 231 162 | 8/1987 |
| EP | 2 072 026 | 6/2009 |
| WO | WO 2010/150016 | 12/2010 |

OTHER PUBLICATIONS

Moretz W. Ossiculoplasty with an intact stapes: superstructure versus footplate prosthesis placement. The Laryngoscope Nov. 1998; 108: 1-12.
Dornhoffer, J. & Gardner, E.: Prognostic factors in ossiculoplasty: a statistical staging system. Otology & Neurotology 2001; 22: 299-304.

(Continued)

*Primary Examiner* — Thomas J Sweet
*Assistant Examiner* — Krutanjali M Shah
(74) *Attorney, Agent, or Firm* — Michael J. Striker

(57) ABSTRACT

An auditory ossicle prosthesis (10) with a sound transmitting prosthesis body (13) has first and second coupling elements (11, 12) provided at opposite ends. A stabilizer element (14) fixes the prosthesis on a level with the plane of the tympanic membrane and stabilizes the position of the prosthesis in the middle ear. A fixation part (14.2) anchors the Y-shaped stabilizer element at one or more places of the ear canal wall. The fixation part includes two hooked anchoring elements (16) that secure the fixation part in artificially drilled holes in the ear canal wall. The auditory ossicle prosthesis has a particularly simple and compact design and stays spatially fixed within very small variations in its initial position after implantation inside the middle ear cavity, providing effective protection against post-operative dislocation, tilting or tipping and without deteriorating sound transmission properties of the prosthesis.

10 Claims, 17 Drawing Sheets

(56) References Cited

OTHER PUBLICATIONS

Albu, S., Babighian, G., Trabalzini, F. Prognostic factors in tympanoplasty. The American Journal of Otology 1998; 19:136:140.
Black B.: Ossiculopasty prognosis: The SPITE method of assessement. The American Journal of Otology. vol. 13, No. 6, Nov. 1992. 544-551.
Fisch U.: Tympanoplasty, Mastoidectomy, and Stapes Surgery. New York: Thiem Medical Publishers, 1994 (abstract & review).
Wehrs R.: The homograft tympanic membrane after 12 years. Ann Otol Rhinol Laryngol Sep.-Oct. 1982; 91:533-7 (abstract).
Black B.: Neomalleous ossiculoplasty. Otology & Neurotology 2002; 23:636-642.
Austin D. F.: Ossicular reconstruction. Otolaryngologic Clinics of North America, No. 1, Feb. 1972; vol. 5:145-160.
Kartusch J. M.: Ossicular chain reconstruction: Capitulum to malleus. Otolaryngol Clin North Am 1994; 27: 689-715.
Vincent R, Sperling N., Oates J., Jindal M.: Surgical findings and long-term hearing results in 3050 stapedotomies for primary otosclerosis: a prospective study with the Otology-Neurology Database. Otology & Neurotology 2006; 27:S25-47.
American Academy of Otolaryngology—Head Neck Surgery Foundation, Inc. Committee on Hearing and Equilibrium guidelines for the evaluation of results of treatment of conductive hearing loss. Otolaryngol Head Neck Surg 1995; 113: 186-7.
Vincent R, Sperling N. M, Oates J., Osborn J.: Ossiculoplasty with intact stapes and absent malleus: the Silastic banding technique. Otology & Neurotology 2005; 26: 846-852.
Austin D.: Transcanal tympanoplasty: a 15-year report. Trans Am Acad Ophtamol Otolaryngol 1976; 82:30-8 (abstract).

\* cited by examiner

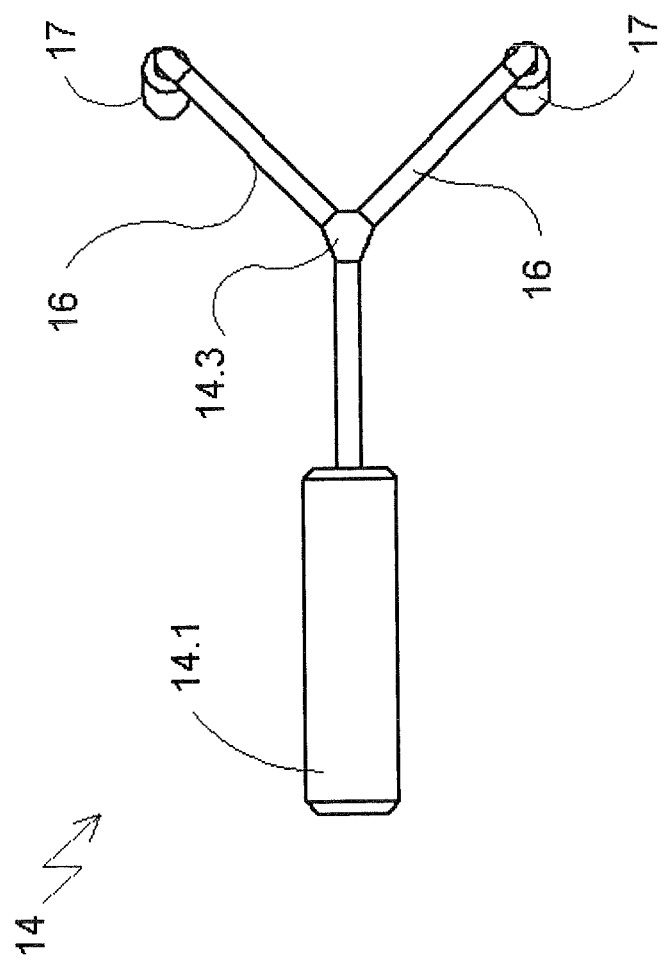

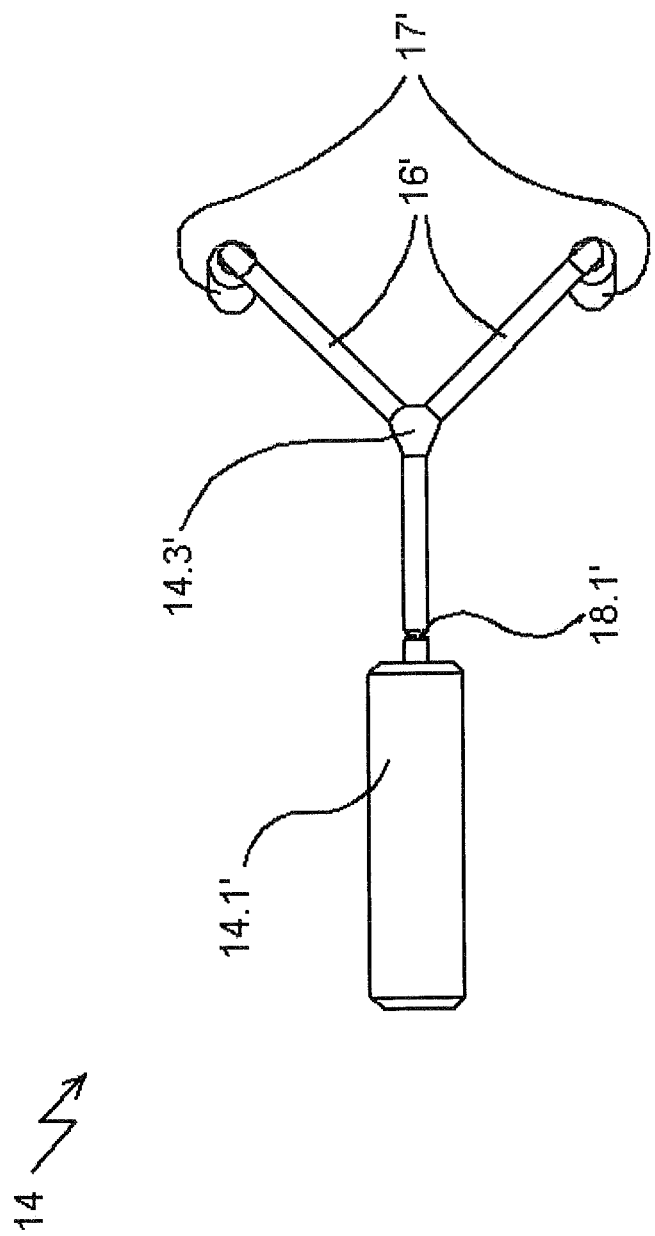

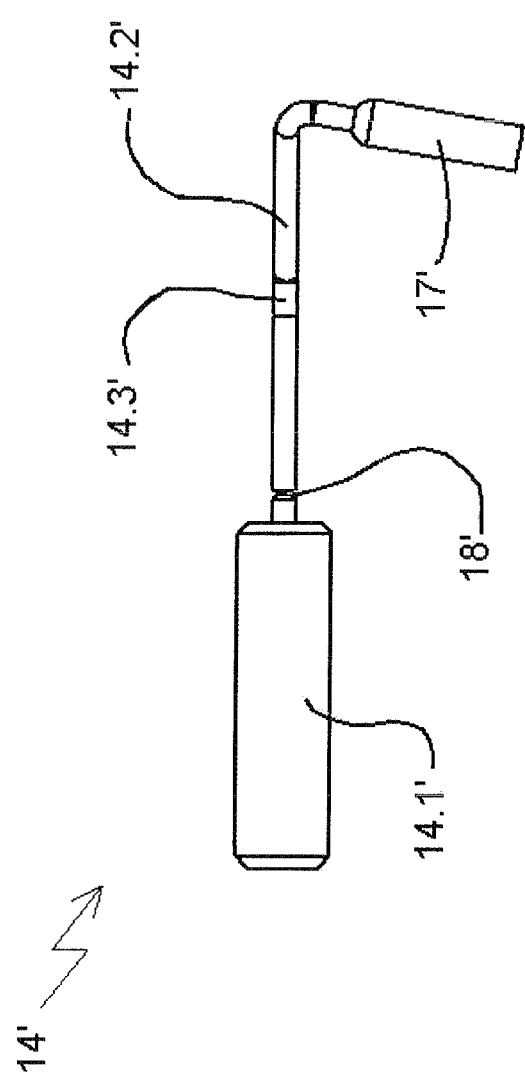

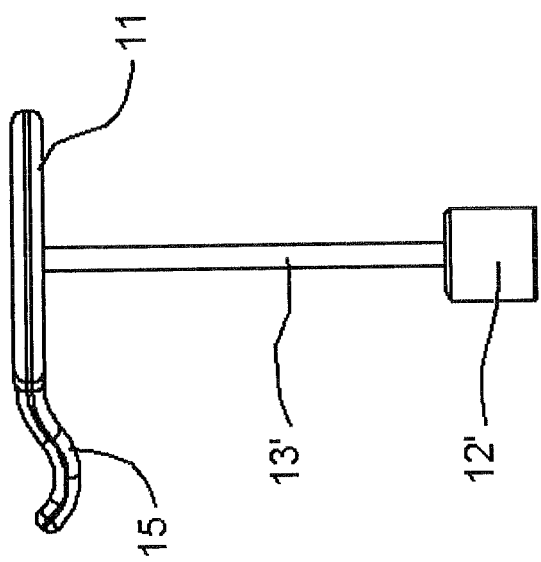

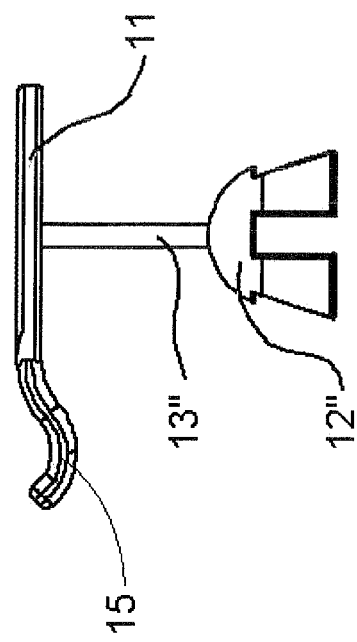

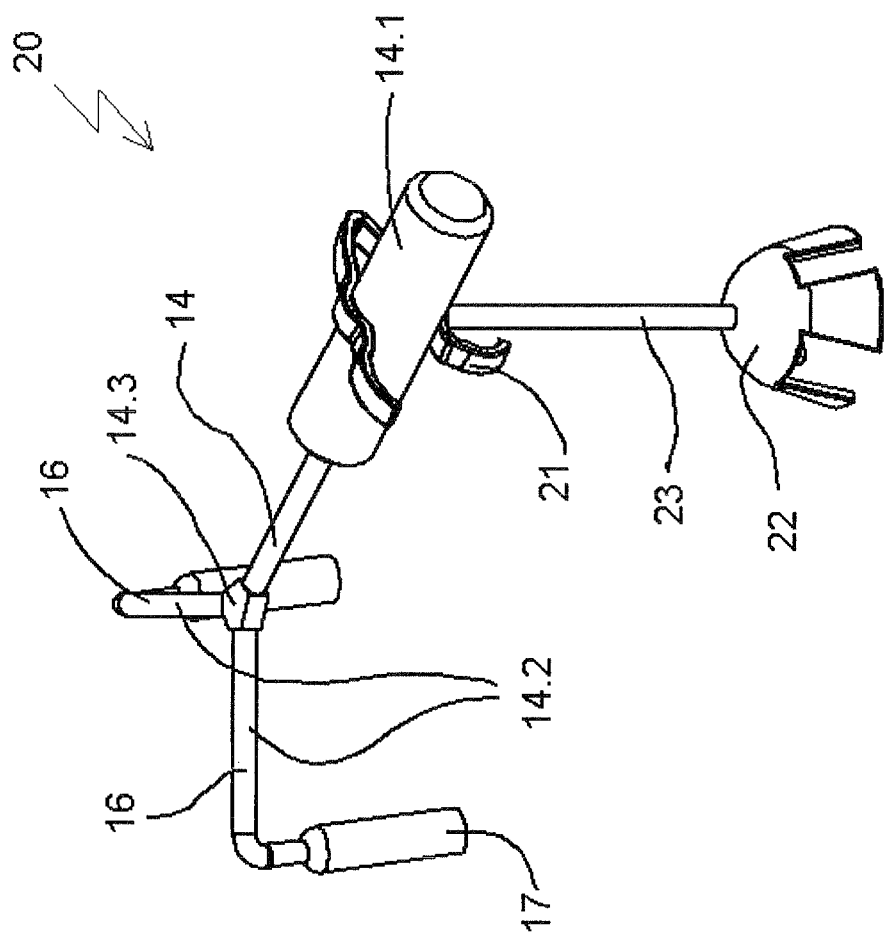

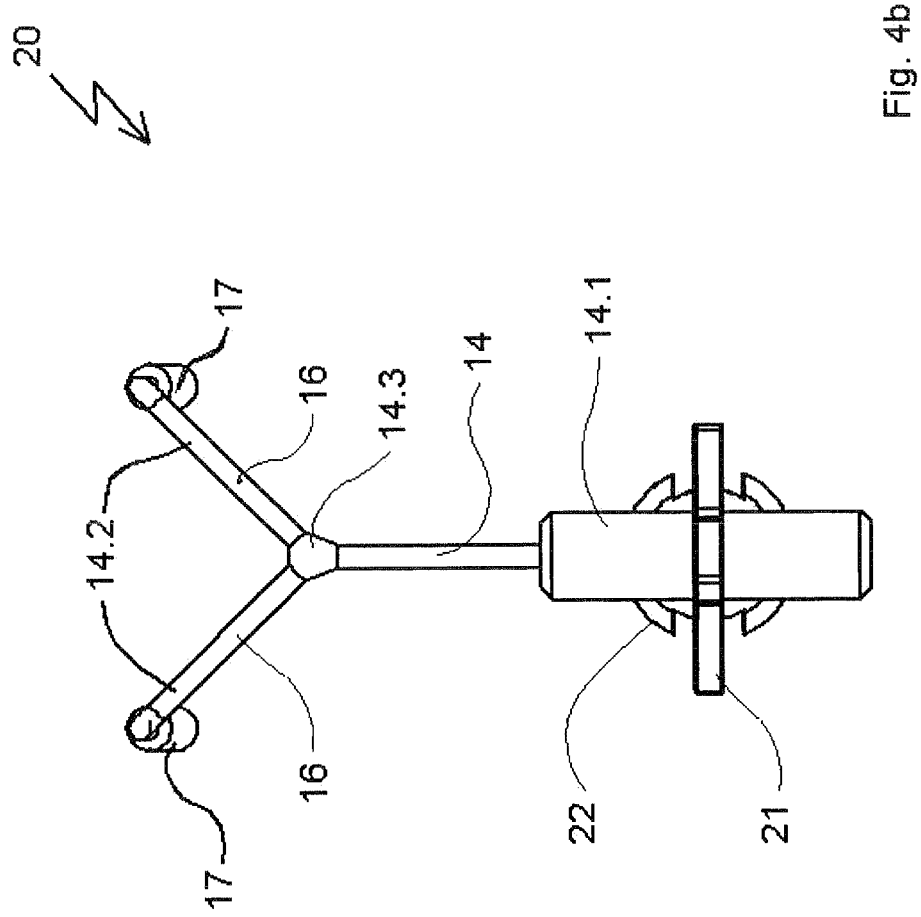

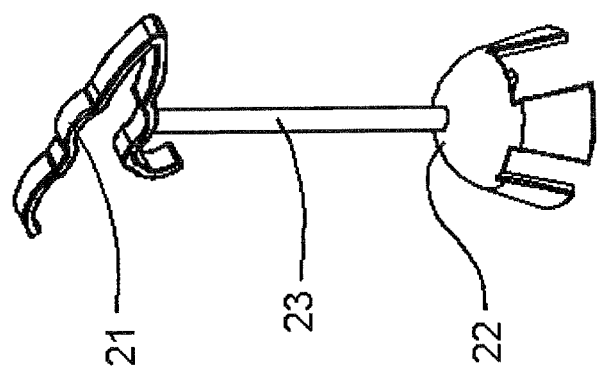

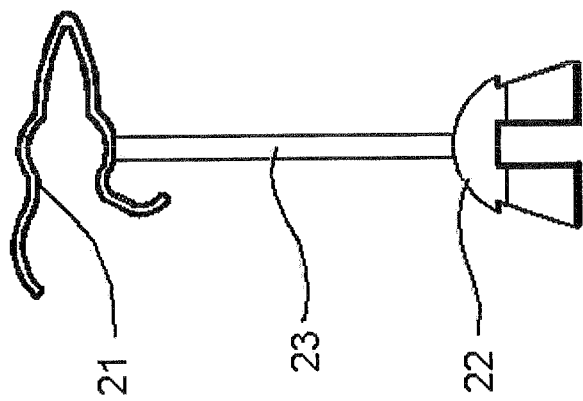

AUDITORY OSSICLE PROSTHESIS WITH STABILISER ELEMENT

BACKGROUND OF THE INVENTION

The present invention relates to an auditory ossicle prosthesis designed for replacing or bridging at least one element in the human auditory ossicle chain with a sound transmitting prosthesis body which at one end has a first coupling element designed as a head plate for mechanical connection of the prosthesis to the tympanic membrane and which at the other end has a second coupling element either designed for mechanical connection of the prosthesis to a second element of the human auditory ossicle chain, in particular to the stapes footplate, or for being inserted directly into the inner ear, whereby a stabiliser element is provided which is designed for fixation of the auditory ossicle prosthesis in its implanted state on a level with the plane of the tympanic membrane and for stabilising the position of the implanted auditory ossicle prosthesis in the middle ear, whereby the stabiliser element is adapted for permanent and stable securing at a section of the prosthesis body adjacent to the first coupling element and comprises a fixation part for anchoring the stabiliser element at one or more places of the ear canal wall.

Devices of this type are described in EP 0 231 162 A1, U.S. Pat. No. 4,130,905, WO 2010/150016 A1 and DE 20 2008 003887 U1.

Similar devices are, for example, described in DE 10 2007 041 539 B4 or US 2009 149 697 A1.

Ossicle prostheses are used in cases in which the ossicles of the human middle ear are missing or damaged, either entirely or partially, to conduct sound from the tympanic membrane to the inner ear. The ossicle prosthesis has two ends. Depending on the specific circumstances, one end of the ossicle prosthesis is fastened to the tympanic membrane, for instance, using a top plate, and the other end of the ossicle prosthesis is fastened, e.g., to the stapes of the human ossicular chain, or it is inserted directly into the inner ear. In many cases, with the known ossicle prostheses, sound conduction between the tympanic membrane and the inner ear is limited, because most known ossicle prostheses do not fully replace the natural anatomical formations of the ossicular chain.

After the prosthesis has been surgically implanted in the middle ear and the tympanic membrane has been closed, the recovery phase begins. Scars form during this period, and they produce unforeseeable forces, which can cause the prosthesis to move out of its initially localized position within the middle ear.

U.S. Pat. No. 4,169,292 A describes a—comparatively exotic—artificial middle ear prosthesis for replacing the complete ear structure from the bony ear canal up to the oval window of the vestibule including a tube to replace at least part of the bony ear canal, an annulus to connect an artificial ear drum to the tube, a complex structure to replace the hammer and anvil of a human patient and a piston means connected to the complex structure to replace at least part of the stirrup. This very complex type of middle ear prostheses requires, however, very extensive operational effort for being implanted, in particular the provision of an artificial ear canal. On the other hand does this type of prostheses not allow for being directly mechanically coupled to the tympanic membrane or anyone of the ossicles.

SUMMARY OF THE INVENTION

In contrast thereto, it is an object of the present invention is to improve a generic auditory ossicle prosthesis of the type described initially, using a particularly simple and compact design and the simplest technical means possible, in a cost-favorable manner by ensuring on the one hand that the auditory ossicle prosthesis stays spatially fixed within very small variations in its initial position after implantation inside the middle ear cavity, in particular providing effective protection against post-operative dislocation, tilting or tipping of the prosthesis and, on the other hand, that the sound transmission properties of the prosthesis are not deteriorated by the mechanical stabilization measures.

According to the present invention, this object is attained in a manner that is surprisingly simple and effective in that the stabiliser element is Y-shaped, whereby the fixation part comprises two hooked anchoring elements adapted for securing the fixation part in artificially drilled holes in the ear canal wall starting from a common bifurcation point at the body of the stabiliser element and branching towards their hooked free ends at an angle with respect to each other.

It is a surprising fact discovered by the inventors, that a fixation of the auditory ossicle prosthesis by using the stabiliser element in accordance with the present invention does just not considerably debase the sound transmission through the prosthesis which one would a-priori expect considering the usual implications of any mechanical fixation. Normally, the stiffening of a device induced by fixing it at one or more points will inevitably reduce its capability of freely swinging and oscillating thereby of course deteriorating the sound transmission properties of the device in its fixated state. This is, however, not true for a device according to the present invention, which is mainly due to the choice of a stabilization point on a level with the plane of the tympanic membrane. Thus, the auditory ossicle prosthesis—despite being spatially fixated by anchoring at one or more points of the ear canal wall—still retains its ability to swing freely following the acoustic amplitudes tapped from the tympanic membrane and thereby transmitting the sound to the inner ear region.

In preferred embodiments of the auditory ossicle prosthesis according to the invention, the first coupling element is designed as a clip-like, umbrella-like or U-shaped part for mechanically coupling the prosthesis to a first element of the human auditory ossicle chain, in particular to the manubrium.

The second coupling element can be designed for mechanical connection of the prosthesis to the stapes head or as a piston for being inserted directly into the inner ear.

Further, the stabiliser element can be adapted for permanent and stable securing at the first coupling element.

Preferably, the stabiliser element is completely or partly made of titanium because of its bio-compatible properties.

Alternatively or in addition, the stabiliser element may comprise at least parts made of a material with memory effect, in particular of Nitinol.

In further preferred embodiments the auditory ossicle prosthesis according to the invention is assembled from different modular components allowing for a greater ad hoc flexibility during the implantation operation which is per se known e.g. from EP 2 072 026 B1 or US 2009 164 010 A1.

Other beneficial embodiments are characterised in that the stabiliser element comprises at least one predetermined breaking point or a portion of a material thickness less than the material thickness of the prosthesis body which allows for an easy mechanical decoupling of the stabiliser element from the prosthesis at any time after the implantation. Moreover; a particularly thin design of the stabiliser element contributes to excellent swinging properties and thus to good sound transmission qualities.

In a class of embodiments of the auditory ossicle prosthesis according to the invention, the stabiliser element comprises a clipping element for securing the stabiliser element at the first coupling element or at a section of the prosthesis body adjacent to the first coupling element.

An alternative class of embodiments is characterised in that the stabiliser element comprises an elongated portion functionally replacing the natural malleus handle.

In modifications of these embodiments which are easy to manufacture, the elongated part may be shaped as a piston.

Other modifications of these embodiments are characterised in that the auditory ossicle prosthesis comprises a receiving section designed for supporting the stabiliser element in the implanted state of the auditory ossicle prosthesis.

These modifications can be further improved by a receiving section comprising a hook shaped portion provided at the first coupling element.

Embodiments of the auditory ossicle prosthesis according to the present invention are very advantageous in which the fixation part comprises more hooked anchoring elements adapted for securing the fixation part in more artificially drilled holes in the ear canal wall.

Variants of the above-described embodiments are ergonomically particularly favorable in which the hooked anchoring elements comprise reinforced free end portions.

From the preceding discussion it is clear that also a stabiliser element per se being designed for fixating an auditory ossicle prosthesis in its implanted state on a level with the plane of the tympanic membrane and for stabilising the position of the implanted auditory ossicle prosthesis in the middle ear, whereby the stabiliser element is adapted for permanent and stable securing at the first coupling element or at a section of the prosthesis body adjacent to the first coupling element and comprises a fixation part for anchoring the stabiliser element at one or more places of the ear canal wall, falls within the scope of the present invention, as long as the stabiliser element is Y-shaped, whereby the fixation part comprises two hooked anchoring elements adapted for securing the fixation part in artificially drilled holes in the ear canal wall starting from a common bifurcation point at the body of the stabiliser element and branching towards their hooked free ends at an angle with respect to each other.

Further features and advantages, of the present invention result from the detailed description of embodiments of the invention presented below with reference to the figures in the drawing which shows the details that are essential to the present invention. Further features and advantages of the present invention also result from the claims. The individual features may be realized individually, or they may be combined in any possible manner in different variants of the present invention.

Embodiments of the present invention are depicted in the schematic drawing and are described in greater detail in the description that follows. The embodiments of auditory prostheses in FIGS. 3a through 5b are only illustrative and not claimed per stabiliser element as invention. Also, the surgical methods referred in the description are not part of the present invention.

BRIEF DESCRIPTION OF THE DRAWINGS

FIG. 2a shows a view in greater detail of the stabiliser element of FIG. 1b with a piston-shaped elongated part.

FIG. 2c shows a view of a stabiliser element like in FIG. 2a, but with a predetermined breaking point.

FIG. 2d shows a view of the stabiliser element of FIG. 2c seen from the side.

FIG. 3d shows a view of the prosthesis of FIG. 3c seen from the side.

FIG. 3f shows a view of the prosthesis of FIG. 3e seen from the side.

FIG. 4a shows a schematic, spatial depiction of a further embodiment of the invention with a partial auditory ossicle prosthesis having a first coupling element designed as clip for gripping an end of the stabiliser element, a second coupling element formed as a sliced bell for being mounted on the stirrup and the stabiliser element according to FIG. 2a.

FIG. 4b shows a view of the embodiment of FIG. 4a from above in a direction perpendicular to the plane of the head plate.

FIG. 5a shows a view of the partial auditory ossicle prosthesis of FIG. 4a in a schematic, spatial depiction.

FIG. 5b shows a view of the prosthesis of FIG. 5a seen from the side.

DESCRIPTION OF THE PREFERRED EMBODIMENTS

Figure 1A:
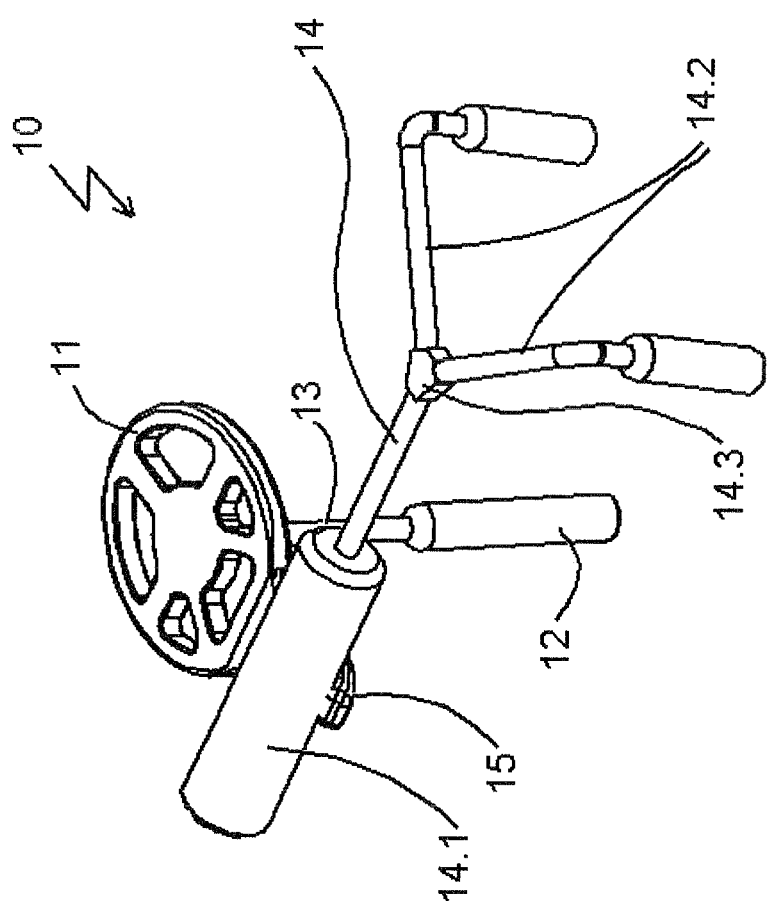
FIG. 1a shows a schematic, spatial depiction of a first embodiment of the invention with a total auditory ossicle prosthesis having a first coupling element designed as a head plate for laying on the tympanic membrane, a second coupling element formed as a piston for being inserted directly into the inner ear and a stabiliser element for anchoring in the ear canal wall.
Figure 1B:
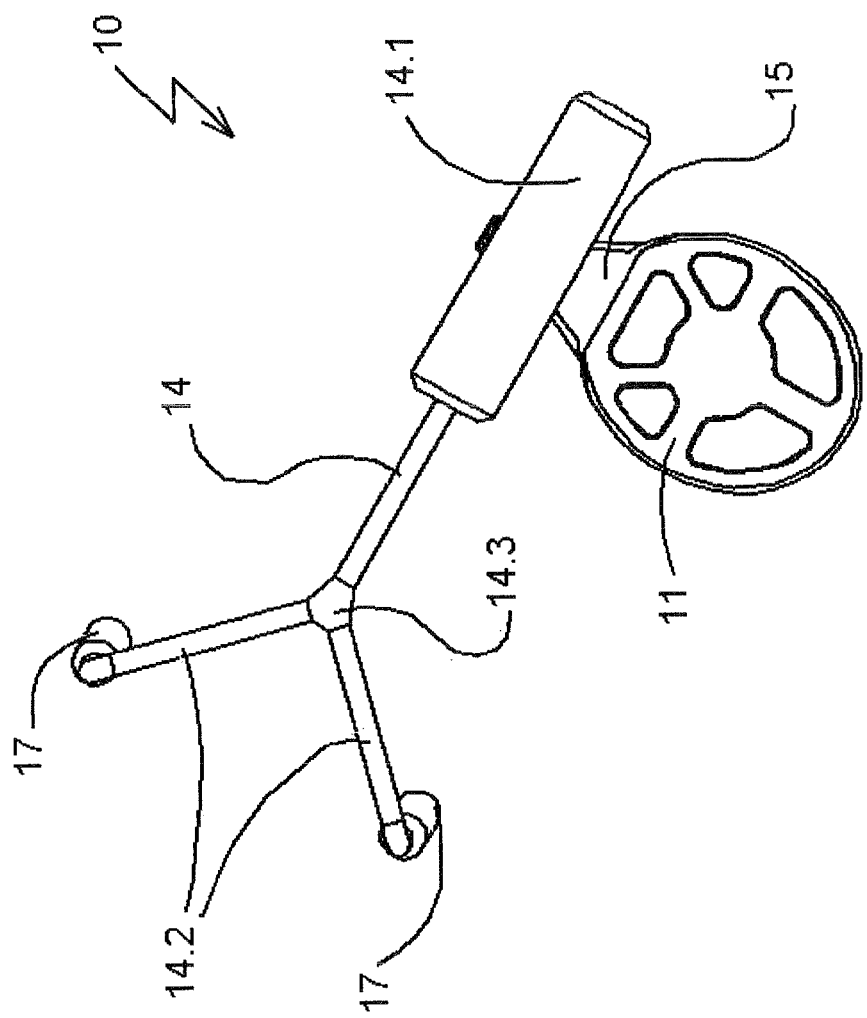
FIG. 1b shows a view of the embodiment of FIG. 1a from above in a direction perpendicular to the plane of the head plate.

The embodiments of an auditory ossicle prosthesis 10; 20 depicted in a schematic, spatial manner in FIGS. 1a, 1b, 4a and 4b of the drawing, are designed for replacing or bridging at least one element in the human auditory ossicle chain with a sound transmitting prosthesis body 13; 13'; 13"; 23 which at one end has a first coupling element 11; 21 designed either as a head plate for mechanical connection of the prosthesis to the tympanic membrane or as a clip-like, umbrella-like or U-shaped part for mechanically coupling the prosthesis to a first element of the human auditory ossicle chain, in particular to the manubrium, and which at the other end has a second coupling element 12; 12'; 12"; 22 either designed for mechanical connection of the prosthesis to a second element of the human auditory ossicle chain, in particular to the stapes head or to the stapes footplate, or designed as a piston for being inserted directly into the inner ear.

The present invention is characterised in that a stabiliser element 14; 14'; 24 is provided which is designed for fixation of the auditory ossicle prosthesis 10; 20 in its implanted state on a level with the plane of the tympanic membrane and for stabilising the position of the implanted auditory ossicle prosthesis 10; 20 in the middle ear, whereby the stabiliser element 14; 14'; 24 may comprise titanium and/or a material with memory effect, in particular of Nitinol and is adapted for permanent and stable securing at the first coupling element 11; 21 or at a section of the prosthesis body 13; 13'; 13"; 23 adjacent to the first coupling element 11; 21 and comprises a fixation part 14.2; 14.2'; 24.2 for anchoring the stabiliser element 14; 14'; 24 at one or more places of the ear canal wall.

As also shown in the embodiments of figures is through 2e, 4a and 4b, the fixation part 14.2; 14.2'; 24.2 can comprise one or more hooked anchoring elements 16; 16'; 26 having reinforced free end portions 17; 17'; 27 adapted for securing the fixation part 14.2; 14.2'; 24.2 in one or more artificially drilled holes in the ear canal wall. In particular, the stabiliser element 14; 14'; 24 may be Y-shaped, whereby the fixation part 14.2; 14.2'; 24.2 comprises two hooked anchoring elements 16; 16'; 26 starting from a common bifurcation point 14.3; 14.3'; 24.3 at the body of the stabiliser element 14; 14'; 24 and branching towards their hooked free ends at an angle with respect to each other.

In the embodiments of the invention shown in figures is through 2d, 4a and 4b, the stabiliser element 14; 14' comprises an elongated part 14.1; 14.1' shaped as a piston and functionally replacing the natural malleus handle. Accordingly, embodiments of the auditory ossicle prosthesis 10 as shown in FIGS. 1a, 1b and 3a through 3f can comprise a receiving section 15 with a hook shaped portion provided at the first coupling element 11 designed for supporting the elongated part 14.1; 14.1' of the stabiliser element 14; 14' in the implanted state of the auditory ossicle prosthesis 10.

In further embodiments of the invention, like in those shown in FIGS. 4a through 5b, the first coupling element 21 can have a clip-like design for being fixed on the elongated part 14.1 of the stabiliser element 14. In these embodiments, the stabiliser element 14 and in particular its piston-like elongated part 14.1 may carry a sound transmitting coupling link to the tympanic membrane, which will in most practical cases comprise a tailor-made element made from the patient's natural cartilage.

Figure 2B:
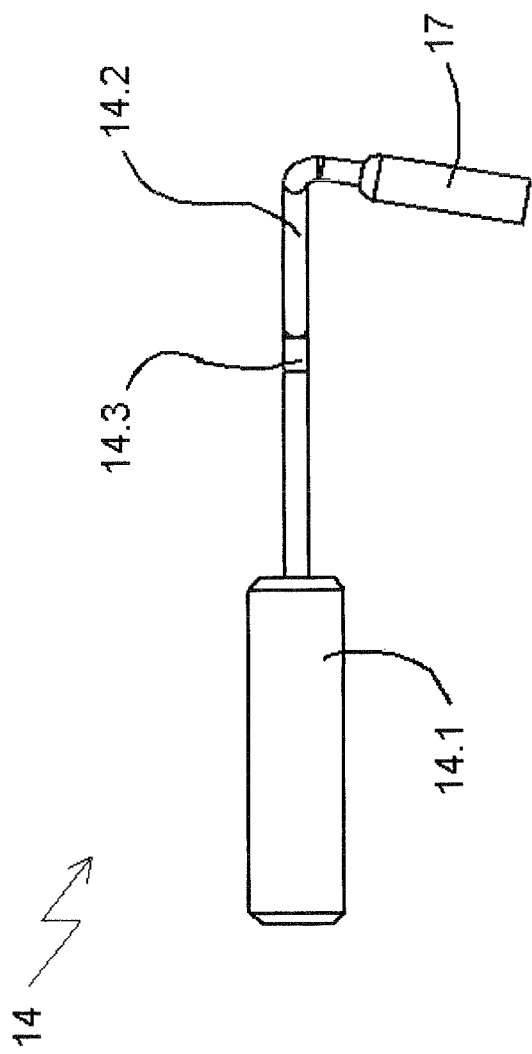
FIG. 2b shows a view of the stabiliser element of FIG. 2a seen from the side.
Figure 2E:
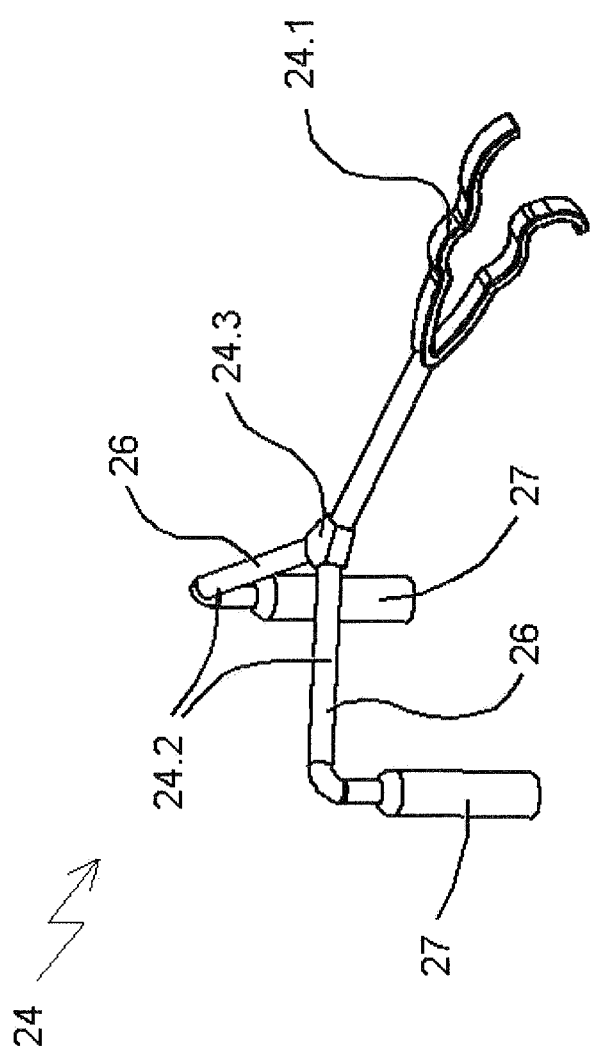
FIG. 2e shows a schematic, spatial depiction of a stabiliser element with clipping element for securing the stabiliser element at the first coupling element of the prosthesis or at a section of the prosthesis body adjacent to the first coupling element.
Figure 3A:
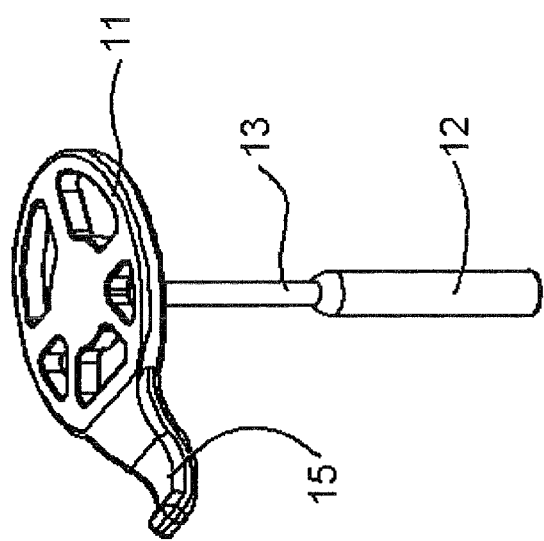
FIG. 3a shows a view of the total auditory ossicle prosthesis of FIG. 1a in a schematic, spatial depiction.
Figure 3B:
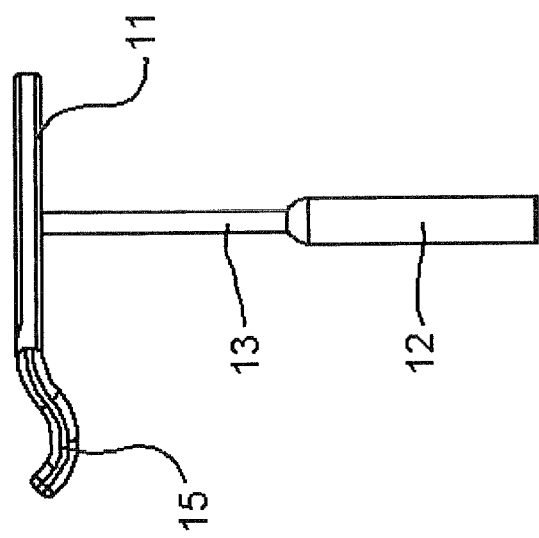
FIG. 3b shows a view of the prosthesis of FIG. 3a seen from the side.
Figure 3C:
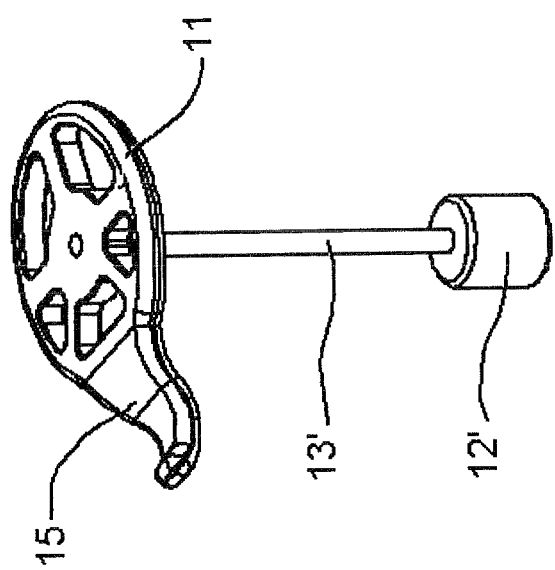
FIG. 3c shows a view of an embodiment of a partial auditory ossicle prosthesis with a head plate and a plunger-like second coupling element in a schematic, spatial depiction.
Figure 3E:
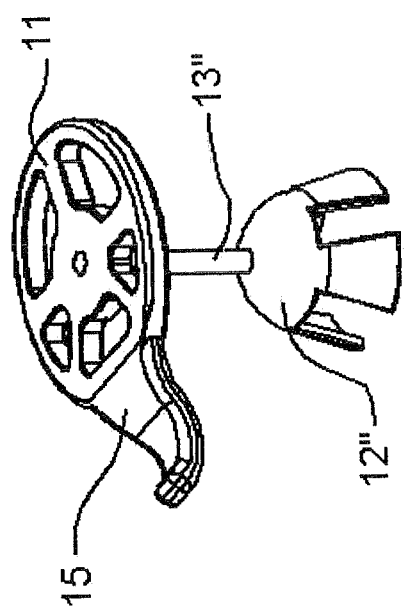
FIG. 3e shows a view of an embodiment of a partial auditory ossicle prosthesis with a head plate and a sliced bell as a second coupling element in a schematic, spatial depiction.

Another class of embodiments of the invention can comprise a stabiliser element 24 as depicted in FIG. 2e having a clipping element 24.1 for securing the stabiliser element 24 at the first coupling element of the auditory ossicle prosthesis or at a section of the prosthesis body 13; 13'; 13"; 23 adjacent to the first coupling element.

FIGS. 2c and 2d show a variant of the stabiliser element 14' according to the invention comprising at least one predetermined breaking point 18'. The same effect can be achieved in other embodiments—not shown in the drawings—having a portion of a material thickness less than the material thickness of the prosthesis body 13; 13'; 13"; 23.

In still further embodiments of the invention not depicted in the present drawings, the auditory ossicle prosthesis according to the invention may be assembled from different modular components.

The auditory ossicle prosthesis 10; 20 according to the present invention is generally designed as a MRP (=Malleus Replacement Prosthesis) for a better stability.

The absence of the malleus handle can affect hearing results after ossiculoplasty. To enhance middle ear prosthesis stability, recreation of an absent malleus can be important.

In close conjunction with Robert Vincent MD from Beziers, France (Causse Ear Clinic), KURZ has developed a new concept of Tympanoplasty.

The MRP (Malleus Replacement Prosthesis) is a titanium neo-malleus which is implanted underneath the tympanic membrane at any position in the bony rim. It is attached via a Y-shaped titanium wire with two hooks. These hooks are inserted into two holes, which are drilled with a 0.6 mm burr into the external canal wall. The surgeon introduces the MRP and can connect almost any Partial- or Total-Replacement Prosthesis due to the malleable MRP.

The primary advantage of this new concept is to keep the neo-malleus in proper position during the initial healing period, reducing the risk of tilting.

Benefits:
Higher stability of ossicular chain reconstruction
Pure titanium for highest biocompatibility
Easy and safe procedure
A truly versatile prosthesis which can be used in most cases The MRP implantation requires drilling two holes to create space for the MRP hooks. The direction for drilling the holes is determined by the status of the EAC (=external auditory canal). When there is enough bone at the posterior superior part of the EAC the holes are drilled approximately at 09 and 11 o'clock for a right ear and 1 and 3 o'clock for a left ear to leave room for the first and second hook respectively. When there is not enough residual posterior-superior bony canal wall it is possible to drill the holes through the posterior-inferior bony canal wall. Thus, the position of the titanium neo-malleus will be exactly opposite to the position of a normal malleus handle.

MRP can be used in all cases of malleus absence (Austin-Kartush Groups C and D). There might be a persistent atticotomy and not enough residual bone at the posterior-superior part of the EAC. Therefore the MRP should be implanted in the posterior-inferior part of the EAC (6 to 8 o'clock).

Two holes are drilled through the EAC wall at 6 and 8 o'clock from side to side with a 0.6 mm diamond dust burr to create space for the hooks of the MRP. The distance between the two EAC holes is equal to the distance between the hooks of the MRP. Drilling of the holes requires highly regulated speed with constant irrigation to prevent burning or pressure necrosis of the bone. The hooks of the MRP are inserted into the holes. This configuration prevents MRP displacement and avoids contact between the neo-malleus and the canal wall.

While the MRP is held in position by the hooks the thin titanium link between the handle and the hooks enables the surgeon to easily accommodate the position of the neo-malleus to all anatomical variations. The neo-malleus is slightly moved superiorly and is placed in proper position overlying the stapes Capitulum.

It is possible to insert any type of partial or total prosthesis at the same stage (onestage procedure) which will be positioned from the stapes capitulum or footplate to the handle of the MRP. The PORP is placed onto the stapes capitulum. The groove of the prosthesis head is then placed underneath the handle of the MRP.

As with a titanium middle ear prosthesis it is advised to cover the system with a layer of cartilage.

In the following, results of scientific research work performed by Robert Vincent, Causse Ear Clinic, Colombiers (France) pertaining to MRP (=MALLEUS REPLACEMENT PROSTHESES) are presented:

Introduction

The presence or absence of a malleus handle affects results in ossiculoplasty particularly in the absence of a stapes superstructure. Numerous authors have emphasized the importance of the malleus in successful ossiculoplasty (1-4). Recreation of the malleus has been used by several authors to enhance middle ear prosthesis stability (5-7).

During the period of January 1991 to June 2010, 1764 consecutive ossiculoplasty procedures were performed by the author (RV) in the same tertiary referral centre. Of these, 178 cases (10%) cases were performed with malleus absent and stapes present and 74 cases (4%) with malleus and stapes both absent. Of these 74 cases, 18 were operated with a bone anchored malleus prosthesis (MRP) implantation from December 2009 to July 2010.

This study aimed to determine the effectiveness of the MRP which was designed to replace a missing malleus. Any type of partial or total ossicular chain replacement prosthesis can be coupled to the MRP which will enhance the stability of PORPs and TORPs.

Material and Method:

This is a prospective study of 18 patients (18 ears) who were operated from Dec. 12, 2009 to Jun. 28, 2010 with MRP implantation. All cases were revision tympanoplasty cases for CSOM without active cholesteatoma.

One patient was also implanted with a MRP for revision otosclerosis with eroded incus and malleus. This patient is excluded from this preliminary study.

Assessment of hearing status was conducted before and 3 months after surgery. The mean age was 41 years (age range 16-66 yr). Sex Ratio was 72% female (13 cases) and 28% male 28% (5 cases).

The ossicular chain status was explored at the time of surgery and cases were assigned on 4 groups according to the status of the ossicular chain. Austin's classification of ossicular defects as modified by Kartush was used to define the ossicular status encountered (8, 9).

Austin-Kartush group D (malleus and stapes absent): 15 cases

Austin-Kartush group C (malleus absent, stapes present): 1 case—Austin-Kartush group B (malleus present, stapes absent): 1 case—Austin-Kartusk group F (stapes fixed, malleus absent): 1 case All cases were revision tympanoplasty cases and the cause of failure was identified as displaced prosthesis in all cases. None of these cases required tympanic membrane grafting during the procedure. All cases had intact, healthy middle ear mucosa with no active cholesteatoma or inflammation.

Of these 18 cases, 9 Austin-Kartush group cases (50%) were operated with a simultaneous implantation of a MRP and a TORP which was positioned from the MRP to the stapes footplate during the same operation (one-stage procedure). The remaining 9 cases (50%) were implanted with a MRP only (first-stage procedure) and will be operated for a second stage procedure 3 to 6 months later with a TORP placement from the MRP to the stapes footplate.

The main cause of failure which was identified at the time of surgery was prosthesis displacement in 15 cases and prosthesis extrusion in 3 cases.

All data were tabulated using the Otology-Neurotology Database (ONDB) (AS Multimedia Inc., Cassagne, France) (10). This is a commercially available software package developed at our centre, designed to comply with the American Academy of Otolaryngology guidelines for reporting clinical and audiometric results (11).

Surgical Technique for MRP Implantation:

All procedures were performed by the same surgeon (RV) and a transcanal approach was used in all cases. Two tunnels were drilled through the EAC (=external auditory canal wall) from side to side with a 0.6 mm diamond dust burr to leave room for the two hooks of the MRP. The distance between the 2 EAC tunnels were equal to the distance between the two hooks of the two tunnels of the MRP.

The drilling of the two tunnels required highly regulated speed with constant irrigation to prevent burning or pressure necrosis of the bone.

The choice of the position of these two tunnels were dictated by the status of the EAC. In 17 cases (94%) they were drilled approximately at 11 and 09 o'clock for a right ear and 1 and 3 o'clock for a left ear to leave room for the first and second hook respectively. Thus, the position of the titanium neo-handle of the MRP was slightly more posterior to a normal malleus handle. In one case (6%) there was not enough residual posterior-superior bony canal wall to allow for drilling out the tunnels which were then drilled at 5 and 6 o'clock. Thus, the position of the titanium neo-handle was exactly opposite but parallel to the position of a normal malleus handle.

The two hooks of the MRP were inserted in the two tunnels and the titanium handle was positioned over the stapes footplate. This configuration prevents MRP displacement and avoids contact between the neo-handle and the canal wall. Each hook of the MRP is inserted within its corresponding tunnel and the titanium handle is positioned over the stapes footplate.

While the MRP was kept in position by the 2 hooks the thin titanium link between the handle and the hooks enabled the surgeon to easily accommodate the position of the neo-handle to all anatomical conditions.

It was possible to slightly move the handle laterally, inferiorly or superiorly. The foremost advantage of this prosthesis is to keep the neo-handle in proper position overlying the stapes footplate in all cases.

In 9 cases a TORP was planed to be inserted in the same stage (one-stage procedure). The distance between the neo-malleus of the MRP and the stapes footplate was determined with an elongated stapes measuring rod. The TORP shaft was cut at the appropriate length and the TORP was positioned from the neo-handle to the stapes footplate. The distal tip of the TORP's shaft is centered to the stapes footplate and the MRP's neo-handle is easily introduced within the groove of the TORP's head.

A thin layer of tragal cartilage was interposed over the MRP in all cases covering both the two hooks and the neo-handle.

Audiometric Assessment

Audiometric evaluation included preoperative and postoperative air-bone gap (ABG), air conduction (AC) thresholds, and bone-conduction (BC) thresholds. Only AC and BC results that were obtained at the same time postoperatively were used for calculation of ABG and pure-tone averages (PTAs). We used a four-frequency PTA for AC and BC thresholds (0.5, 1, 2 and 4 kHz) obtained at 3 months follow-up for the one-stage procedure cases (9 case). The preoperative and postoperative BC and AC levels at 4 kHz were also assessed. Audiometry was reported according to American Academy of Otolaryngology-Head and Neck Surgery Guidelines (11) except for thresholds at 3 kHz which were substituted in all cases with those at 4 kHz.

Preliminary Results

Of the 18 cases in which MRP was implanted, 9 cases (50%) were operated with a simultaneous implantation of a MRP and a TORP which was positioned from the MRP to the stapes footplate during the same operation (one-stage procedure).

Preliminary postoperative hearing results were studied for these 9 one-stage procedure cases.

Of the 9 one-stage procedure cases, 5 cases (55.5%) had postoperative audiological data available at 3 months follow-up. Of these 5 cases, one patient had more than 5 previous failed surgeries, 2 patients had 4 previous failed surgeries and 2 patients had one previous failed operation. The main cause of failure which was identified at the time of surgery was prosthesis displacement in 7 cases and prosthesis extrusion in 2 cases.

Hearing result of these 5 cases are presented in Table 1. There was no case of postoperative sensorineural hearing loss in the series and no prosthesis extrusion nor tympanic membrane reaction was observed postoperatively.

TABLE 1

Postoperative hearing results at 3 months in
5 cases (Simultaneous MRP + TORP implantation)

| Variable | MRP + TORP (n = 5) |
|---|---|
| ABG < 10 dB-% | 100 (5 cases) |
| Mean BC-dB | 16.3 |
| Mean AC-dB | 23 |
| Mean ABG-dB | 6.7 |
| SNHL-dB | 0 |

BC, Bone conduction;
AC, air conduction;
ABG, air-bone gap;
SNHL, sensorineural hearing loss The postoperative air bone gap (ABG) (averaged over 0.5, 1, 2 and 4 kHz) was closed to 10 dB in all cases (5 cases, 100%). The postoperative mean ABG was 6.7 dB compared to 39.5 dB preoperatively. The mean postoperative bone conduction (BC) was 16.3 dB compared to 18.8 dB preoperatively. The mean postoperative air conduction (AC) was 23 dB compared to 58 dB preoperatively.

Discussion

Re-creation of the malleus has been used in the past (5-7). Without an intact malleus, Wehrs (6) suggested the use of an homologous drum and malleus, which usually requires staging for a stable reconstruction. Black (7) introduced a technique of neo-malleus ossiculoplasty by using an autograft neo-malleus strut and an assembly rather than columella in cases in which the malleus was unavailable for assembly techniques.

More recently we described an original technique of silastic banding in a consecutive series of 100 cases with missing malleus and intact stapes superstructure (Austin-Kartush group C) (12). Ossiculoplasty was performed with a TORP positioned from the stapes footplate to the under surface of the tympanic membrane, using a silastic band to stabilize the prosthesis.

Our preliminary hearing results with the MRP implantation in cases of missing malleus and stapes are encouraging and compare favourably with the results reported by other authors in case of missing malleus (Table 2).

TABLE 2

Hearing results in case of missing malleus in literature review

| Series | Austin-Kartush Group | Material | n | Postop ABG < 10 dB (%) | Postop mean ABG |
|---|---|---|---|---|---|
| Moretz (1) | C | PORP | 6 | 0 | 24 |
| | C | TORP | 4 | 0 | 24 |
| Vincent (10) | C | TORP | 96 | 66 | 12 |
| Austin (13) | C | Partial autograft | 23 | 12 | 27 |
| Black (14) | C | PORP | 13 | 15 | — |
| Goldenberg (15) | C | PORP | 7 | 14 | 23 |
| Current series | D | TORP | 5 | 100 | 6.7 |

ABG, air-bone gap

Table 3 shows the postoperative comparative hearing results of the author (RV) at 3 months follow-up in case of absence of malleus (Austin-Kartush groups C and D) according to the type of prosthesis used and assembly. Our best short-term hearing results were obtained with the MRP implantation coupled to a TORP: 100% of ABG closure to within 10 dB compare to 57% in Austin-Kartush group C cases with PORP implantation from tympanic membrane (TM) to stapes head (S), 58% in Austin-Kartush group C cases with TORP implantation from TM to footplate (F) and Silastic banding technique and 35.7% in Austin-Kartush group D cases with TORP implantation from TM to F.

TABLE 3

Personal results. Postoperative comparative results at 3 months
in case of absence of malleus: Austin Kartush groups C and D.

| | Austin-Kartush group | | Austin-Kartush group D | |
|---|---|---|---|---|
| Prosthesis | PORP | TORP + Silastic Banding | TORP | MRP + TORP |
| Assembly | TM/S | TM/F | TM/F | TM/F |
| Available data | 7 | 106 | 28 | 5 |
| ABG < 10 dB-% | 57 (4 cases) | 58 (61 cases) | 35.7 (10 cases) | 100 (5 cases) |
| ABG < 20 dB-% | 86 (6 cases) | 77 (81 cases) | 50 (14 cases) | 100 |
| Mean BC-dB | 28.4 | 24.2 | 30.5 | 16.3 |
| Mean AC-dB | 41 | 37 | 53.5 | 23 |
| Mean ABG-dB | 12.6 | 12.9 | 23 | 6.7 |
| SNHL-dB | 0 | 0 | 0 | 0 |

BC, Bone conduction;
AC, air conduction;
ABG, air-bone gap;
SNHL, sensorineural hearing loss;
TM/S, tympanic membrane to stapes head assembly;
TM/F, tympanic membrane to footplate assembly.

Moreover these preliminary results tend to show better results when a prosthesis is implanted from the titanium handle of the MRP then from the normal malleus handle. This may be related to the vibratory properties of the MRP. This factor is currently under research study at the Otolaryngology Department of Hannover Medical University (Prof Med Thomas Lenarz, Dr Med Gentiana Wenzel). The results of this research study may dramatically increase the indication of use of the MRP in the future.

Because of the osseointegration of Titanium, the MRP may become fixed with time to the bony canal wall as the bone may grow on to the surface of the two hooks in the tunnels. However thanks to the vibratory properties of the MRP which may be related to its specific design the vibratory properties of the neo-handle may remain stable and efficient. This is also under current study at the Otolaryngology Department of Hannover Medical University.

CONCLUSION

The MRP was developed to improve on results of cases with absent malleus that had been previously managed with columellae or neo-malleus technique or silastic banding in case of stapes present.

With the MRP a new malleus handle is re-created which can be used with any type of PORP or TORP which can be positioned under the neo-handle in a single or two-stage procedure. This decreases the risk of displacement of PORP and TORP.

The amount of time required to place a MRP will vary depending on the experience of the practitioner, the quality and quantity of the bone of the external auditory canal and the difficulty of the individual situation but the surgical technique is simple and reliable.

The preliminary results of this current series has demonstrated successful ABG closure in 100% of case. However, considering the short period of follow-up of the present series it will be important to prospectively observe outcomes after longer period of follow-up.

BIBLIOGRAPHY

1—Moretz W. Ossiculoplasty with an intact stapes: superstructure versus footplate prosthesis placement. Laryngoscope 1998; 108:1-12
2—Dornhoffer J, Gardner E. Prognostic factors in ossiculoplasty: a statistical staging system. Otol Neurotol 2001; 22:299-304
3—Albu S, Babighian G, Trabalzini F. Prognostic factors in tympanoplasty. Am J Otol 1998; 19:136-40
4—Black R. Ossiculoplasty prognosis: The SPITE method of assessment. Am J Otol 1992; 13:544-51
5—Fisch U. Tympanoplasty, Mastoidectomy, and Stapes Surgery. New York: Thieme Medical Publishers, 1994
6—Wehrs R. The homograft tympanic membrane after 12 years. Ann Otol Rhinol Laryngol 1982; 91:533-7
7—Black B. Neomafleus ossiculoplasty. Otol Neurotol 2002; 23:636-42
8. Austin D F. Ossicular reconstruction. Otolaryngol Clin North Am 1972; 5:145-60.
9. Kartush J M. Ossicular chain reconstruction: Capitulum to malleus. Otolaryngol Clin North Am 1994; 27:689-715.
10—Vincent R, Sperling N, Oates J, Jindal M. Surgical findings and long-term hearing results in 3050 stapedotomies for primary otosclerosis: a prospective study with the Otology Neurotology Database. Otol Neurotol 2006; 27:S25-47
11. American Academy of Otolaryngology-Head Neck Surgery Foundation, Inc. Committee on Hearing and Equilibrium guidelines for the evaluation of results of treatment of conductive hearing loss. Otolaryngol Head Neck Surg 1995; 113:186-7.
12. Vincent R, Sperling N M, Oates J, Osborne J. Ossiculoplasty with intact stapes and absent malleus: the Silastic banding technique. Otol Neurotol 2005; 26:846-852.
13—Austin D. Transcanal tympanoplasty: A 15-year report. Trans Am Acad Ophtalrnol Otolaryngol 1976; 82:30-8

The invention claimed is:

1. An auditory ossicle prosthesis designed for replacing or bridging at least one element in a human auditory ossicle chain with a sound transmitting prosthesis body having a first coupling element at one end designed as a head plate defining a plane for mechanical connection of the prosthesis to the tympanic membrane and a second coupling element at the other end that is either designed for mechanical connection of the prosthesis to a second element of the human auditory ossicle chain or for insertion directly into the inner ear,
   wherein a stabiliser element is provided for fixation of the auditory ossicle prosthesis in an implanted state on a level with the plane of the tympanic membrane and for stabilising a position of the implanted auditory ossicle prosthesis in the middle ear,
   wherein the stabiliser element is adapted for permanent and stable securing at a section of the prosthesis body adjacent to the first coupling element and comprises a fixation part for anchoring the stabiliser element at one or more places of the ear canal wall;
   wherein the stabiliser element is Y-shaped; and
   wherein the fixation part comprises two hooked anchoring elements adapted for securing the fixation part in artificially drilled holes in the ear canal wall, the anchoring elements starting from a common bifurcation point at the body of the stabiliser element and symmetrically branching towards their hooked free ends at an angle with respect to each other, thereby defining a plane parallel or identical to said plane of said head plate, that the hooked anchoring elements comprise reinforced free end portions protruding at an angle from said plane defined by branching anchoring elements, that the stabiliser element comprises an elongated part functionally replacing the natural malleus handle, that the auditory ossicle prosthesis comprises a receiving section designed for supporting the stabiliser element in the implanted state of the auditory ossicle prosthesis and, that the receiving section comprises a hook shaped portion provided at the first coupling element.

2. Auditory ossicle prosthesis according to claim 1, wherein the second coupling element is designed for mechanical connection of the prosthesis to a stapes head or as a piston for insertion directly into the inner ear.

3. Auditory ossicle prosthesis according to claim 1, wherein the stabiliser element is adapted for permanent and stable securing at the first coupling element.

4. Auditory ossicle prosthesis according to claim 1, wherein stabiliser element is completely or partly made of titanium.

5. Auditory ossicle prosthesis according to claim 1, wherein the stabiliser element is completely or partly made of a material with memory effect.

6. Auditory ossicle prosthesis according to claim 1, wherein the prosthesis is assembled from different modular components.

7. Auditory ossicle prosthesis according to claim 1, wherein the stabiliser element comprises at least one predetermined breaking point or a portion of a material thickness less than the material thickness of the prosthesis body.

8. Auditory ossicle prosthesis according to claim 1, wherein the elongated part is shaped as a piston.

9. Auditory ossicle prosthesis according to claim 1, wherein the fixation part comprises more hooked anchoring elements adapted for securing the fixation part in artificially drilled holes in the ear canal wall.

10. Auditory ossicle prosthesis according to claim 5, wherein the material is Nitinol.

* * * * *